US012491317B2

(12) United States Patent
Fenlon et al.

(10) Patent No.: US 12,491,317 B2
(45) Date of Patent: Dec. 9, 2025

(54) MEDICAMENT CONTAINER CARRIER AND ADAPTER

(71) Applicant: SANOFI-AVENTIS DEUTSCHLAND GMBH, Frankfurt am Main (DE)

(72) Inventors: Derek Fenlon, Wexford (IE); Pascal Launois, Dublin (IE); Julian McDonnell, County Wicklow (IE); Martina Moyne, County Donegal (IE); Conor Mulcahy, County Dublin (IE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 0 days.

(21) Appl. No.: 18/957,952

(22) Filed: Nov. 25, 2024

(65) Prior Publication Data

US 2025/0082852 A1 Mar. 13, 2025

Related U.S. Application Data

(63) Continuation of application No. 17/564,354, filed on Dec. 29, 2021, which is a continuation of application
(Continued)

(30) Foreign Application Priority Data

Mar. 14, 2013 (EP) .................................... 13159253

(51) Int. Cl.

| | |
|---|---|
| ***A61M 5/19*** | (2006.01) |
| ***A61J 1/20*** | (2006.01) |
| ***A61M 5/31*** | (2006.01) |

(52) U.S. Cl.
CPC .............. *A61M 5/19* (2013.01); *A61J 1/2096* (2013.01); *A61M 5/3129* (2013.01); *A61J 1/201* (2015.05)

(58) Field of Classification Search
None
See application file for complete search history.

(56) References Cited

U.S. PATENT DOCUMENTS 3,026,873 A 3/1962 Miskel et al.
3,076,455 A 2/1963 McConnaughey et al.
(Continued)

FOREIGN PATENT DOCUMENTS

CA 2212489 A1 2/1998
CN 2745588 Y 12/2005
(Continued)

OTHER PUBLICATIONS

International Preliminary Report on Patentability in International Appln. No. PCT/EP2014/054922, issued on Sep. 15, 2015, 6 pages.
(Continued)

*Primary Examiner* — Manuel A Mendez
(74) *Attorney, Agent, or Firm* — Fish & Richardson P.C.

(57) ABSTRACT

Described is a medicament container carrier adapted to hold a first medicament container having a first predetermined size and capable of containing more than a first volume of a medicament. The container carrier comprises a body, and an adapter coupled to the body. The adapter is adapted to hold a second medicament container having a second predetermined size different from the first predetermined size and capable of containing no more than the first volume of the medicament.

30 Claims, 6 Drawing Sheets

Related U.S. Application Data

No. 14/775,316, filed as application No. PCT/EP2014/054922 on Mar. 13, 2014, now Pat. No. 11,235,102.

(56) References Cited

U.S. PATENT DOCUMENTS 3,144,178 A 8/1964 Sarnoff
3,880,163 A 4/1975 Ritterskamp
4,563,175 A 1/1986 Lafond
4,643,724 A 2/1987 Jobe
4,655,751 A 4/1987 Harbaugh
4,664,653 A 5/1987 Sagstetter et al.
4,735,311 A 4/1988 Lowe et al.
4,838,857 A 6/1989 Strowe et al.
4,871,355 A 10/1989 Kikkawa
4,909,791 A 3/1990 Norelli
4,931,040 A 6/1990 Haber et al.
4,946,447 A 8/1990 Hardcastle et al.
4,964,866 A 10/1990 Szwarc
4,973,318 A 11/1990 Holm et al.
4,990,142 A 2/1991 Hoffman et al.
4,997,422 A 3/1991 Chow et al.
5,000,744 A 3/1991 Hoffman et al.
5,078,698 A 1/1992 Stiehl et al.
5,085,641 A 2/1992 Sarnoff et al.
5,163,918 A 11/1992 Righi et al.
5,169,392 A 12/1992 Ranford et al.
5,281,198 A 1/1994 Haber et al.
5,282,793 A 2/1994 Larson
5,290,255 A 3/1994 Vallelunga et al.
5,320,609 A 6/1994 Haber et al.
5,322,511 A 6/1994 Armbruster et al.
5,344,407 A 9/1994 Ryan
5,350,367 A 9/1994 Stiehl et al.
5,356,395 A 10/1994 Chen
5,368,578 A 11/1994 Covington et al.
5,383,858 A 1/1995 Reilly et al.
5,383,863 A 1/1995 Mardones
5,439,450 A 8/1995 Haedt
5,451,214 A 9/1995 Hajishoreh
5,480,387 A 1/1996 Gabriel et al.
5,520,653 A 5/1996 Reilly et al.
5,599,309 A 2/1997 Marshall et al.
5,637,101 A 6/1997 Shillington
5,709,662 A 1/1998 Olive et al.
5,779,675 A 7/1998 Uber et al.
5,865,805 A 2/1999 Ziemba
5,913,844 A * 6/1999 Ziemba ............. A61M 5/14546 604/154
5,925,032 A 7/1999 Clements
5,928,205 A 7/1999 Marshall
5,928,698 A 7/1999 Soyad
6,059,756 A 5/2000 Yeh
6,090,082 A 7/2000 King et al.
6,203,530 B1 3/2001 Stewart
6,210,369 B1 4/2001 Wilmot et al.
6,371,939 B2 4/2002 Bergens et al.
6,409,701 B1 6/2002 Cohn et al.
6,454,743 B1 9/2002 Weber
6,544,234 B1 4/2003 Gabriel
6,613,022 B1 9/2003 Doyle
6,656,163 B1 12/2003 Marshall et al.
6,726,657 B1 4/2004 Dedig et al.
6,743,205 B2 6/2004 Nolan, Jr. et al.
7,118,552 B2 10/2006 Shaw et al.
7,288,078 B2 10/2007 Fitzgerald
7,449,012 B2 11/2008 Young et al.
7,597,685 B2 10/2009 Olson
7,717,877 B2 5/2010 Lavi et al.
7,918,824 B2 4/2011 Bishop et al.
7,955,303 B2 6/2011 Burren et al.
8,409,138 B2 * 4/2013 James ................. A61M 5/2033 604/110
8,647,299 B2 2/2014 Stamp
8,734,394 B2 5/2014 Admas et al.
8,845,594 B2 9/2014 Jennings
8,876,785 B2 11/2014 Holmqvist
8,900,197 B2 12/2014 Crow
8,992,746 B2 3/2015 Miyaji et al.
9,044,553 B2 6/2015 James et al.
9,072,833 B2 7/2015 Jennings et al.
9,180,259 B2 11/2015 Lesch, Jr.
9,216,256 B2 12/2015 Olson et al.
9,233,213 B2 1/2016 Olson et al.
9,242,053 B2 1/2016 Wozencroft
9,289,554 B2 3/2016 Hourmand et al.
9,402,957 B2 8/2016 Adams et al.
9,408,970 B2 8/2016 Hourmand et al.
9,408,976 B2 8/2016 Olson et al.
9,713,678 B2 7/2017 Hourmand et al.
9,757,520 B2 9/2017 Corrigan
9,867,940 B2 1/2018 Holmqvist et al.
9,872,961 B2 1/2018 Fourt et al.
10,118,001 B2 11/2018 Fourt et al.
10,314,981 B2 6/2019 Sampson et al.
10,350,362 B2 7/2019 Dennis, Jr. et al.
10,363,377 B2 7/2019 Atterbury et al.
10,420,898 B2 9/2019 Daniel
10,434,258 B2 10/2019 Hourmand et al.
10,441,719 B2 10/2019 Hourman et al.
10,569,019 B2 2/2020 Hirschel et al.
10,646,656 B2 5/2020 Hourmand et al.
10,799,647 B2 10/2020 Hosteettler et al.
10,881,799 B2 1/2021 Hirschel et al.
10,918,803 B2 2/2021 Kemp et al.
11,103,649 B2 8/2021 Kemp et al.
11,298,462 B2 4/2022 Atterburg et al.
11,383,044 B2 7/2022 Tschirren et al.
11,400,221 B2 8/2022 Hourmand et al.
11,400,222 B2 8/2022 Hourmand et al.
11,400,223 B2 8/2022 Hourmand et al.
11,406,763 B2 8/2022 Hourmand et al.
11,406,764 B2 8/2022 Hourmand et al.
11,452,821 B2 9/2022 Lafever et al.
11,511,043 B2 11/2022 Hourmand et al.
12,036,392 B1 7/2024 Fenlon et al.
2001/0005781 A1 6/2001 Bergens et al.
2001/0011163 A1 8/2001 Nolan, Jr. et al.
2002/0045866 A1 4/2002 Sadowski et al.
2002/0083564 A1 7/2002 James
2003/0105430 A1 6/2003 Lavi et al.
2004/0039336 A1 2/2004 Amark et al.
2004/0108339 A1 6/2004 Hansen et al.
2005/0020979 A1 1/2005 Westbye et al.
2005/0027255 A1 2/2005 Lavi et al.
2005/0075602 A1 4/2005 Cherif-Cheikh et al.
2005/0075608 A1 4/2005 Holdgate et al.
2005/0101919 A1 5/2005 Brunnberg
2005/0115507 A1 6/2005 Halachmi et al.
2005/0165353 A1 7/2005 Pessin
2005/0277896 A1 12/2005 Messerli et al.
2006/0036216 A1 2/2006 Rimlinger et al.
2006/0151049 A1 7/2006 Nemoto
2006/0161114 A1 7/2006 Perot et al.
2006/0167412 A1 7/2006 Marshall
2006/0184133 A1 8/2006 Pessin
2007/0173770 A1 7/2007 Stamp
2007/0260348 A1 11/2007 Gordils
2008/0147003 A1 6/2008 Menzi et al.
2008/0228143 A1 9/2008 Stamp
2008/0262427 A1 10/2008 Hommann
2008/0269692 A1 10/2008 James et al.
2009/0012471 A1 1/2009 Harrison
2009/0105663 A1 4/2009 Brand et al.
2009/0254027 A1 10/2009 Moeller
2010/0152655 A1 6/2010 Stamp
2010/0179507 A1 7/2010 Hess et al.
2010/0185178 A1 7/2010 Sharp et al.
2011/0125100 A1 5/2011 Schwirtz et al.
2011/0190693 A1 8/2011 Takatsuka et al.
2012/0053528 A1 3/2012 Bollenbach et al.
2012/0130321 A1 5/2012 Woehr
2012/0186075 A1 7/2012 Edginton

(56) References Cited

U.S. PATENT DOCUMENTS

| | | | |
|---|---|---|---|
| 2012/0203186 | A1 | 8/2012 | Vogt et al. |
| 2012/0209092 | A1 | 8/2012 | Alexandersson |
| 2012/0209192 | A1 | 8/2012 | Alexandersson |
| 2013/0220869 | A1 | 8/2013 | Klintenstedt et al. |
| 2014/0243753 | A1 | 8/2014 | Bostrom |
| 2014/0249479 | A1 | 9/2014 | Pfrang |
| 2014/0323985 | A1 | 10/2014 | Hourmand et al. |
| 2014/0330203 | A1 | 11/2014 | McLoughlin et al. |
| 2014/0330213 | A1 | 11/2014 | Hourmand et al. |
| 2014/0336590 | A1 | 11/2014 | Hourmand et al. |
| 2014/0336592 | A1 | 11/2014 | Hourmand et al. |
| 2018/0064875 | A1 | 3/2018 | Holmqvist |
| 2018/0140781 | A1 | 5/2018 | Kemp et al. |
| 2018/0140782 | A1 | 5/2018 | Kemp et al. |
| 2018/0256822 | A1 | 9/2018 | Hourmand et al. |
| 2019/0201628 | A1 | 7/2019 | Hourmand et al. |
| 2019/0201629 | A1 | 7/2019 | Hourmand et al. |
| 2019/0374717 | A1 | 12/2019 | Swanson et al. |
| 2020/0405960 | A1 | 12/2020 | Hourmand et al. |
| 2020/0405961 | A1 | 12/2020 | Hourmand et al. |
| 2021/0077743 | A1 | 3/2021 | Kemp et al. |
| 2021/0346604 | A1 | 11/2021 | Hourmand et al. |
| 2022/0016358 | A1 | 1/2022 | Kemp et al. |
| 2022/0054755 | A1 | 2/2022 | Hourmand et al. |
| 2022/0054756 | A1 | 2/2022 | Hourmand et al. |
| 2022/0054757 | A1 | 2/2022 | Hourmand et al. |
| 2022/0054758 | A1 | 2/2022 | Hourmand et al. |
| 2024/0207517 | A1 | 6/2024 | Fenlon et al. |

FOREIGN PATENT DOCUMENTS

| | | | |
|---|---|---|---|
| CN | 1911467 | A | 2/2007 |
| CN | 1977986 | A | 6/2007 |
| CN | 2925504 | Y | 7/2007 |
| CN | 101022841 | A | 8/2007 |
| CN | 101400393 | A | 4/2009 |
| CN | 101420995 | A | 4/2009 |
| CN | 201213944 | Y | 4/2009 |
| CN | 101479004 | A | 7/2009 |
| CN | 102014993 | A | 4/2011 |
| CN | 102112168 | A | 6/2011 |
| CN | 103945879 | A | 7/2014 |
| DE | 202009009119 | U1 | 12/2009 |
| EA | 012008 | B1 | 6/2009 |
| EA | 013934 | B1 | 8/2010 |
| EP | 0518416 | A1 | 12/1992 |
| EP | 0692272 | A1 | 1/1996 |
| EP | 1124601 | A1 | 8/2001 |
| EP | 1685865 | A1 | 8/2006 |
| EP | 1702643 | A2 | 9/2006 |
| EP | 1958654 | A1 | 8/2008 |
| EP | 2279771 | A1 | 2/2011 |
| EP | 2438952 | A1 | 4/2012 |
| EP | 2727617 | A1 | 6/2012 |
| EP | 2601992 | A1 | 6/2013 |
| EP | 2777684 | A1 | 9/2014 |
| EP | 2788052 | A1 | 9/2015 |
| EP | 3153197 | A1 | 4/2017 |
| FR | 2764195 | A1 | 12/1998 |
| FR | 2799654 | A1 | 4/2001 |
| GB | 407109 | A | 3/1934 |
| GB | 829724 | A | 3/1960 |
| GB | 1122592 | A | 8/1968 |
| GB | 2388033 | A | 11/2003 |
| GB | 2396298 | A | 6/2004 |
| GB | 2397767 | A | 8/2004 |
| GB | 2447339 | A | 9/2008 |
| GB | 2461084 | A | 12/2009 |
| GB | 2434317 | A | 1/2011 |
| GB | 2471473 | A | 1/2011 |
| JP | H08-10324 | A | 1/1996 |
| JP | 2002-503127 | A | 1/2002 |
| JP | 2002-528182 | A | 9/2002 |
| JP | 2003-511159 | A | 3/2003 |
| JP | 2005-021247 | A | 1/2005 |
| JP | 2005-523121 | A | 8/2005 |
| JP | 2005-536300 | A | 12/2005 |
| JP | 2006-507903 | A | 3/2006 |
| JP | 2006-516901 | A | 7/2006 |
| JP | 2007-511299 | A | 5/2007 |
| JP | 2008-500854 | A | 1/2008 |
| JP | 2009-077943 | A | 4/2009 |
| JP | 2009-518080 | A | 5/2009 |
| JP | 2009-523587 | A | 6/2009 |
| JP | 2009-529395 | A | 8/2009 |
| JP | 2011-156005 | A | 8/2011 |
| JP | 2011-524763 | A | 9/2011 |
| JP | 2014-500086 | A | 1/2014 |
| JP | 2014-500089 | A | 1/2014 |
| RU | 2068708 | C1 | 11/1996 |
| RU | 2172638 | C2 | 8/2001 |
| RU | 2311203 | C2 | 11/2007 |
| RU | 2363500 | C2 | 8/2009 |
| RU | 2012137269 | A | 3/2014 |
| WO | WO 1998/035714 | A1 | 8/1998 |
| WO | WO 1998/056442 | A1 | 12/1998 |
| WO | WO 1999/010030 | A2 | 3/1999 |
| WO | WO 1999/022792 | A1 | 5/1999 |
| WO | WO 2000/024441 | A1 | 5/2000 |
| WO | WO 2001/008727 | A1 | 2/2001 |
| WO | WO 2001/060435 | A1 | 8/2001 |
| WO | WO 2001/093926 | A2 | 12/2001 |
| WO | WO 2002/047746 | A1 | 6/2002 |
| WO | WO 2003/013632 | A2 | 2/2003 |
| WO | WO 2003/068297 | A1 | 8/2003 |
| WO | WO 2003/090822 | A1 | 11/2003 |
| WO | WO 2003/099358 | A2 | 12/2003 |
| WO | WO 2004/007006 | A2 | 1/2004 |
| WO | WO 2004/020026 | A1 | 3/2004 |
| WO | WO 2004/050150 | A2 | 6/2004 |
| WO | WO 2005/001161 | A1 | 1/2005 |
| WO | WO 2005/002650 | A1 | 1/2005 |
| WO | WO 2005/070481 | A1 | 8/2005 |
| WO | WO 2005/083614 | A2 | 9/2005 |
| WO | WO 2005/115506 | A1 | 12/2005 |
| WO | WO 2005/115507 | A1 | 12/2005 |
| WO | WO 2006/047810 | A1 | 5/2006 |
| WO | WO 2006/085176 | A1 | 8/2006 |
| WO | WO 2006/106291 | A1 | 10/2006 |
| WO | WO 2006/106295 | A1 | 10/2006 |
| WO | WO 2007/056792 | A1 | 5/2007 |
| WO | WO 2007/083115 | A1 | 7/2007 |
| WO | WO 2007/104636 | A1 | 9/2007 |
| WO | WO 2007/129106 | A2 | 11/2007 |
| WO | WO 2008/000827 | A1 | 1/2008 |
| WO | WO 2009/019437 | A1 | 2/2009 |
| WO | WO 2009/022132 | A2 | 2/2009 |
| WO | WO 2009/153541 | A2 | 12/2009 |
| WO | WO 2010/072644 | A1 | 7/2010 |
| WO | WO 2010/097116 | A1 | 9/2010 |
| WO | WO 2010/115822 | A2 | 10/2010 |
| WO | WO 2010/136076 | A1 | 12/2010 |
| WO | WO 2010/136077 | A1 | 12/2010 |
| WO | WO 2010/136078 | A1 | 12/2010 |
| WO | WO 2010/147553 | A1 | 12/2010 |
| WO | WO 2011/000570 | A1 | 1/2011 |
| WO | WO 2011/001161 | A1 | 1/2011 |
| WO | WO 2011/101378 | A1 | 8/2011 |
| WO | WO 2011/109205 | A2 | 9/2011 |
| WO | WO 2012/073032 | A1 | 6/2012 |
| WO | WO 2012/089445 | A1 | 7/2012 |
| WO | WO 2012/164403 | A2 | 12/2012 |
| WO | WO 2013/072182 | A1 | 5/2013 |
| WO | WO 2013/083613 | A1 | 6/2013 |
| WO | WO 2013/083614 | A1 | 6/2013 |
| WO | WO 2014/140152 | A1 | 9/2014 |
| WO | WO 2019/074788 | A1 | 4/2019 |

(56) References Cited

FOREIGN PATENT DOCUMENTS

| | | | |
|---|---|---|---|
| WO | WO 2020/190529 | A1 | 9/2020 |
| WO | WO 2021/008839 | A1 | 1/2021 |

OTHER PUBLICATIONS

International Search Report and Written Opinion in International Appln. No. PCT/EP2014/054922, mailed on Apr. 1, 2014, 10 pages.

* cited by examiner

MEDICAMENT CONTAINER CARRIER AND ADAPTER

CROSS-REFERENCE TO RELATED APPLICATIONS

This application is a continuation application of U.S. application Ser. No. 17/564,354, filed on Dec. 29, 2021, which is a continuation application of U.S. application Ser. No. 14/775,316, filed on Sep. 11, 2015, now U.S. Pat. No. 11,235,102, which is a U.S. national stage application under 35 USC § 371 of International Application No. PCT/EP2014/054922, filed on Mar. 13, 2014, which claims priority to European Patent Application No. 13159253.7, filed on Mar. 14, 2013, the entire contents of which are incorporated herein by reference.

TECHNICAL FIELD

The invention relates to an adapter for a medicament container carrier.

BACKGROUND OF THE INVENTION

In a conventional medicament delivery device (e.g., an autoinjector), a pre-filled medicament container (e.g., syringe) is housed in a carrier which is axially movable to achieve needle penetration in an injection site and, optionally, needle withdrawal. A conventional carrier is typically sized and shaped to retain a medicament container of a predetermined size. In order to increase a dose that can be administered by the delivery device, a larger carrier would be necessary to accommodate a larger medicament container. However, a size and shape of the delivery device may not provide space for the larger medicament container. Thus, an entirely different delivery device may be necessary for different dosage amounts.

Accordingly, there is a need for a carrier and an adapter that allows the carrier to accommodate medicament containers of various sizes.

SUMMARY OF THE INVENTION

It is an object of the present invention to provide a medicament container carrier and an adapter for the medicament container carrier.

In an exemplary embodiment, a medicament container carrier adapted to hold a first medicament container having a first predetermined size and capable of containing more than a first volume of a medicament according to the present invention comprises a body, and an adapter coupled to the body. The adapter is adapted to hold a second medicament container having a second predetermined size different from the first predetermined size and capable of containing no more than the first volume of the medicament.

In an exemplary embodiment, the first volume is approximately 2 mL.

In an exemplary embodiment, the adapter includes a distal rib adapted to abut a distal end of the second medicament container.

In an exemplary embodiment, the adapter includes at least one opening providing visual access to the second medicament container.

In an exemplary embodiment, the adapter includes at least one resilient arm adapted to engage the second medicament container. The arm includes a first ramp adapted to engage a distal face of a flange to deflect the arm in a first radial direction. The arm includes a first abutment surface adapted to engage the flange to prevent rotation of the second medicament container relative to the adapter and a second abutment surface adapted to engage the flange to prevent axial displacement of the second medicament container relative to the adapter. The arm includes a second ramp adapted to engage an engagement element on the body to deflect the arm in a second radial direction. The arm includes a third abutment surface adapted to abut a proximal stop in the body to prevent axial displacement of the adapter relative to the body, and a fourth abutment surface adapted to engage a restricting surface in the body to prevent rotation of the adapter relative to the body. The proximal stop is formed in an aperture on the body.

In an exemplary embodiment, the first medicament container and the second medicament container are each one of a pre-filled syringe and a medicament cartridge.

In an exemplary embodiment, a medicament delivery device according to the present invention comprises a housing, and a medicament container carrier according to the exemplary embodiments described herein. The medicament container carrier may be slidably disposed in the housing.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, do not limit the present invention, and wherein.

Corresponding parts are marked with the same reference symbols in all figures.

DETAILED DESCRIPTION

Figure 1:
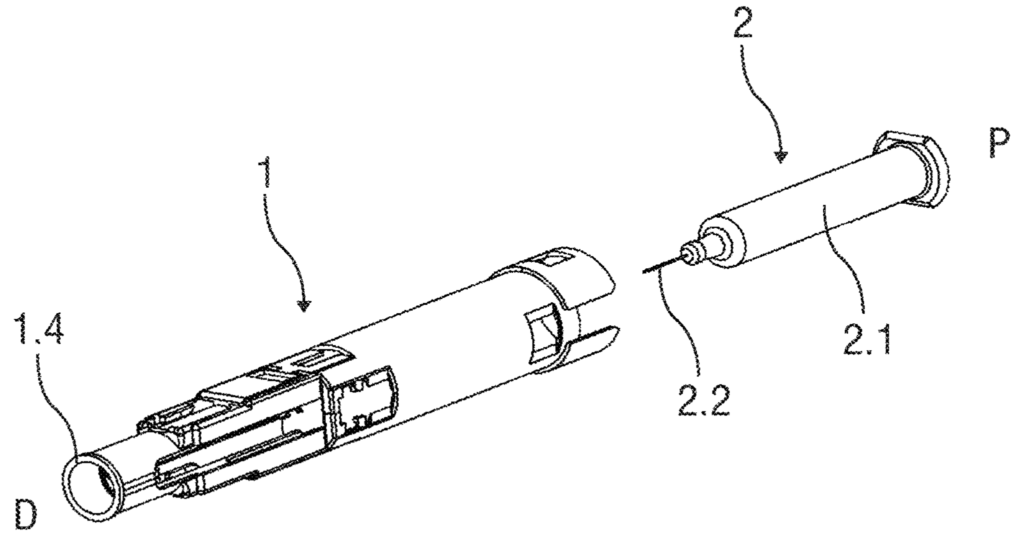
FIG. 1 is a schematic perspective exploded view of an exemplary embodiment of a container carrier and a first medicament container according to the present invention.

FIG. 1 is a schematic perspective exploded view of an exemplary embodiment of a container carrier 1 having a body adapted to hold a first medicament container 2 according to the present invention. The first medicament container 2, which may be a syringe, an ampoule, a cartridge, etc., has a first predetermined size (e.g., length, diameter, etc.) and contains up to a first maximum amount of a medicament. For example, the first medicament container 2 may be a prefilled syringe containing a 2 mL dose of a medicament.

In an exemplary embodiment, the first medicament container 2 comprises a medicament container body 2.1, a needle 2.2 mounted to a distal end of the medicament container body 2.1 and in fluid communication with a cavity defined within the medicament container body 2.1 for containing a medicament, and a stopper (not illustrated) disposed within the cavity near a proximal end of the medicament container body 2.1, wherein the stopper proximally seals the cavity and can be axially displaced within the cavity for expelling the medicament through the needle 2.2. The needle 2.2 may fixed to the container body 2.1 or may be removably coupled thereto. In the latter exemplary embodiment, the needle 2.2 may be a double-tipped needle and the distal end of the body 2.1 may include a septum which receives a proximal tip of the needle 2.2. In the figures, "D" refers to the distal direction, and "P" refers to the proximal direction.

Figure 2:
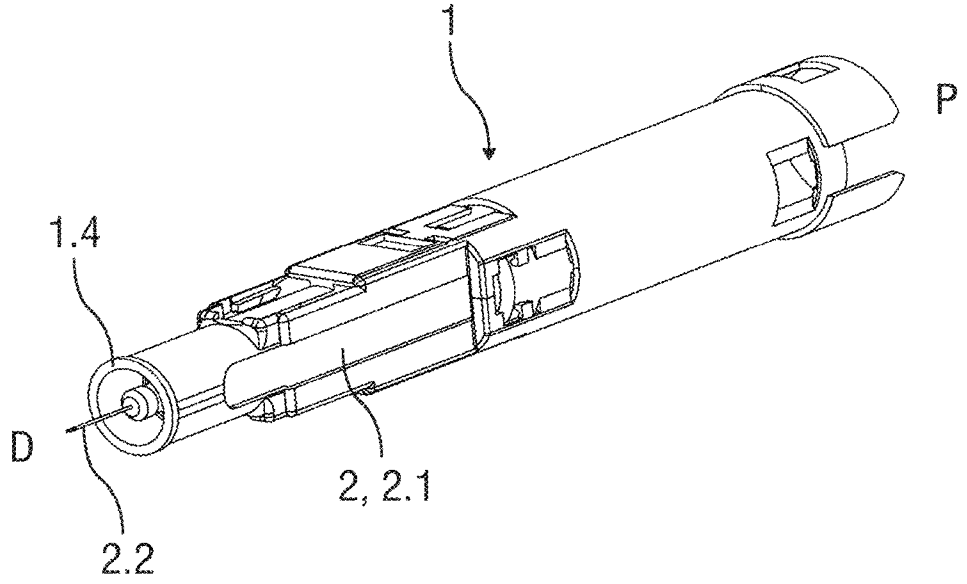
FIG. 2 is a schematic perspective view of an exemplary embodiment of a container carrier coupled to a first medicament container according to the present invention.

FIG. 2 is a schematic perspective view of an exemplary embodiment of the container carrier 1 with the first medicament container 2 coupled thereto. The first medicament container 2 may be inserted into a proximal opening of the container carrier 1 and moved distally until it abuts a distal stop. A retention mechanism (e.g., snaps, clips, locks, etc.) in the container carrier 1 may engage a proximal end (e.g., flange(s)) of the first medicament container 2 to prevent the first medicament container 2 from translating axially relative to the container carrier 1 and/or rotating relative to the container carrier 1.

Figure 3:
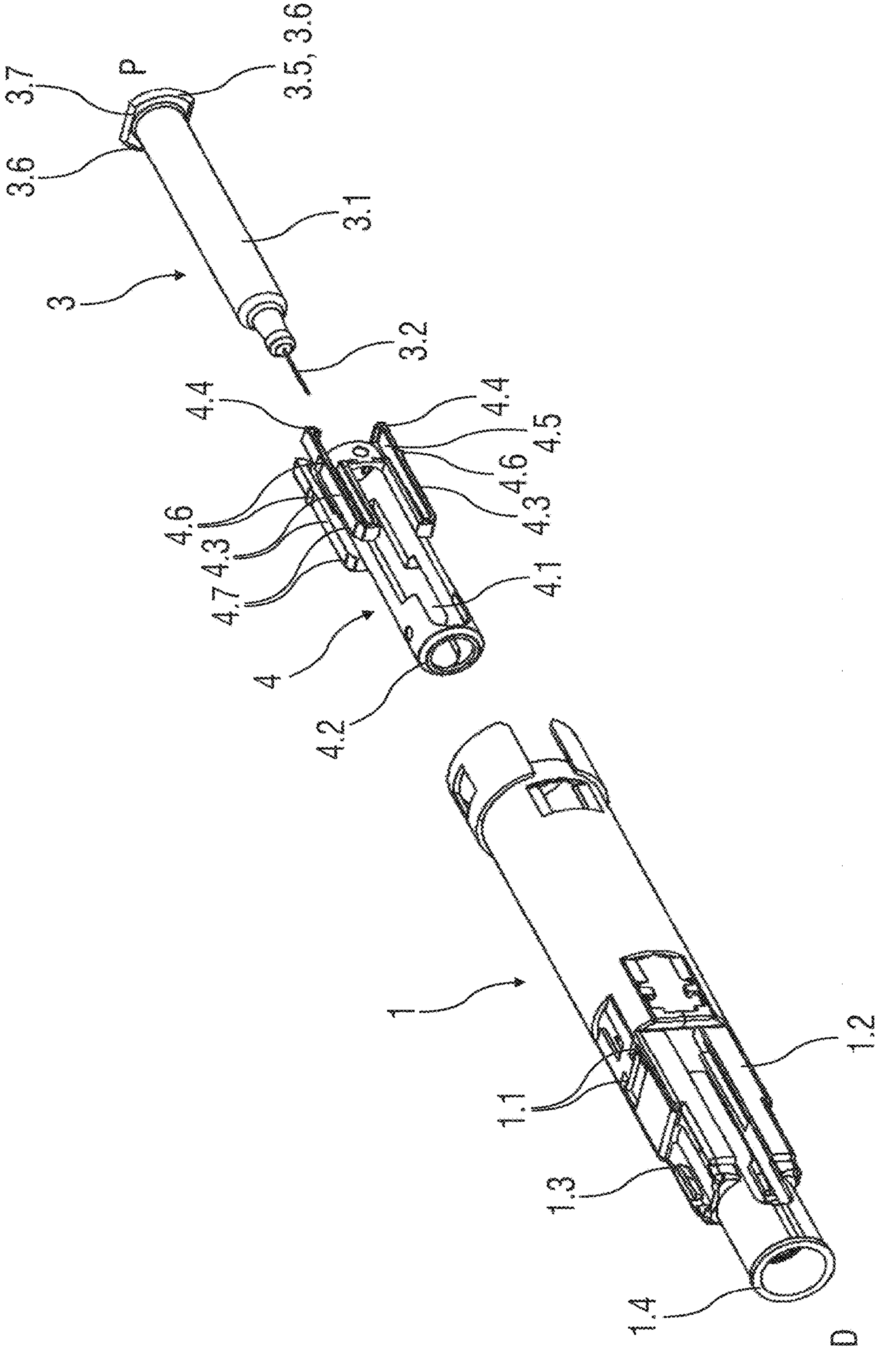
FIG. 3 is a schematic perspective exploded view of an exemplary embodiment of a container carrier, an adapter and a second medicament container according to the present invention.
Figure 4:
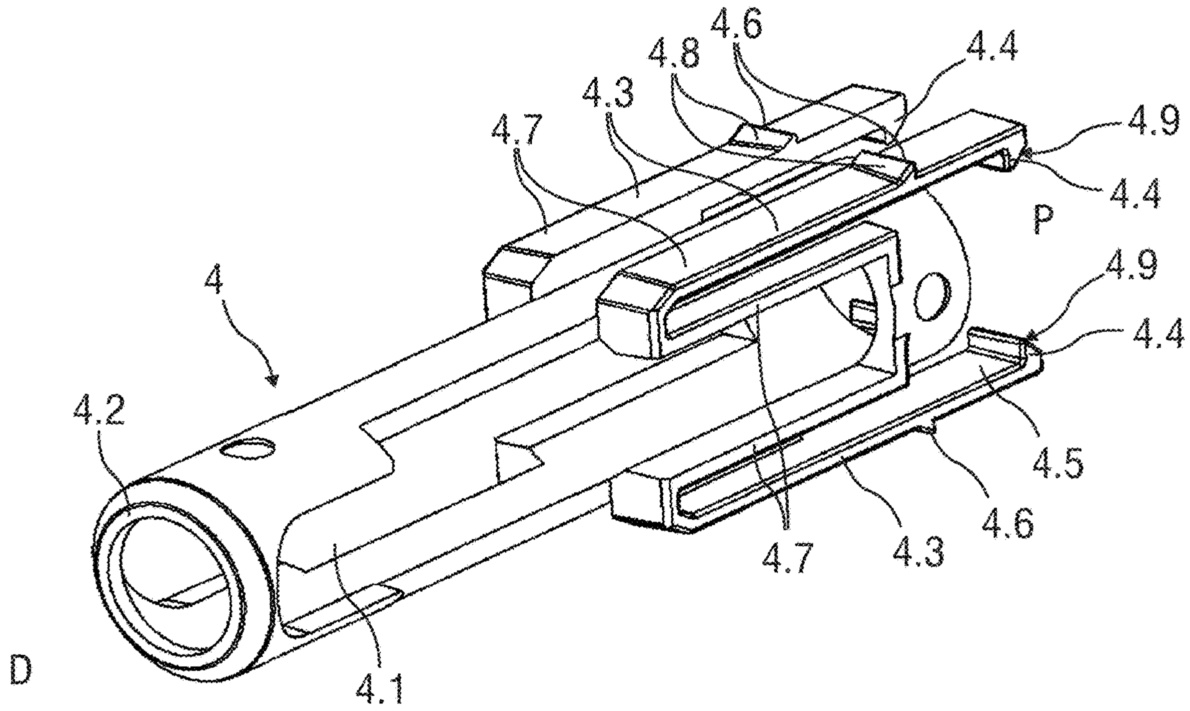
FIG. 4 is a schematic perspective view of an exemplary embodiment of an adapter according to the present invention.

FIG. 3 is a schematic perspective exploded view of an exemplary embodiment of the container carrier 1, an adapter 4 and a second medicament container 3. FIG. 4 is a schematic perspective view of an exemplary embodiment of the adapter 4.

In an exemplary embodiment, the adapter 4 is designed to engage a second medicament container 3 having a second predetermined size smaller than the first predetermined size of the first medicament container 2. The adapter 4 may further be designed to engage the container carrier 1. The second medicament container 3 comprises a medicament container body 3.1, a needle 3.2 mounted to a distal end of the medicament container body 3.1 and in fluid communication with a cavity defined within the medicament container body 3.1 for containing a medicament, and a stopper (not illustrated) disposed within the cavity near a proximal end of the medicament container body 3.1, wherein the stopper proximally seals the cavity and can be axially displaced within the cavity for expelling the medicament through the needle 3.2. The needle 3.2 may fixed to the container body 3.1 or may be removably coupled thereto. In the latter exemplary embodiment, the needle 3.2 may be a double-tipped needle and the distal end of the body 3.1 may include a septum which receives a proximal tip of the needle 3.2. A flange 3.5 may be arranged at a proximal end of medicament container body 3.1. In an exemplary embodiment, the flange 3.5 comprises two arc sections 3.6 connected by two straight sections 3.7.

In an exemplary embodiment, the adapter 4 may be used to allow a medicament delivery device (e.g., a pen injector, an auto-injector, etc.) to accommodate various medicament container sizes. The adapter 4 may allow the usage of a common delivery device for different medicament container sizes. Therefore, a reduction in device costs and consistency in medicament administration may be achieved.

In an exemplary embodiment, the adapter 4 is adapted to retain the second medicament container 3 such that the second medicament container 3 is axially and rotationally fixed within the adapter 4. The adapter 4 is also adapted to be retained within the container carrier 1 such that the adapter 4 is axially and rotationally fixed within the container carrier 1. Preventing rotation of the second medicament container 3 prevents the needle 3.2 from rotating during an injection thus reducing the risk for bending and distorting the needle 3.2 which may otherwise result in pain. Preventing axial movement of the medicament container 3 in a proximal direction P also prevents the second medicament container 3 from being pushed in the proximal direction P relative to the adapter 4 and the container carrier 1 upon contact of the needle 3.2 with an injection site.

In an exemplary embodiment as shown in FIG. 4, the adapter 4 may be sized and/or shaped to telescopically engage the container carrier 1 and the second medicament container 3. For example, the adapter 4 may have an outer geometry which corresponds to an inner shape of the container carrier 1 and an inner geometry which corresponds to the second predetermined size/shape of the second medicament container 3. A distal rib 4.2 formed on a distal end of the adapter 4 may be adapted to abut the distal end of the container body 3.1 to prevent distal movement of the second medicament container 3 beyond the distal rib 4.2.

In an exemplary embodiment, the adapter 4 may include one or more lateral openings 4.1 for allowing inspection of the contents and state of the second medicament container 3. In another exemplary embodiment, the adapter 4 may be made from a transparent/translucent material to provide visual access to the contents of the second medicament container 3.

Figure 5:
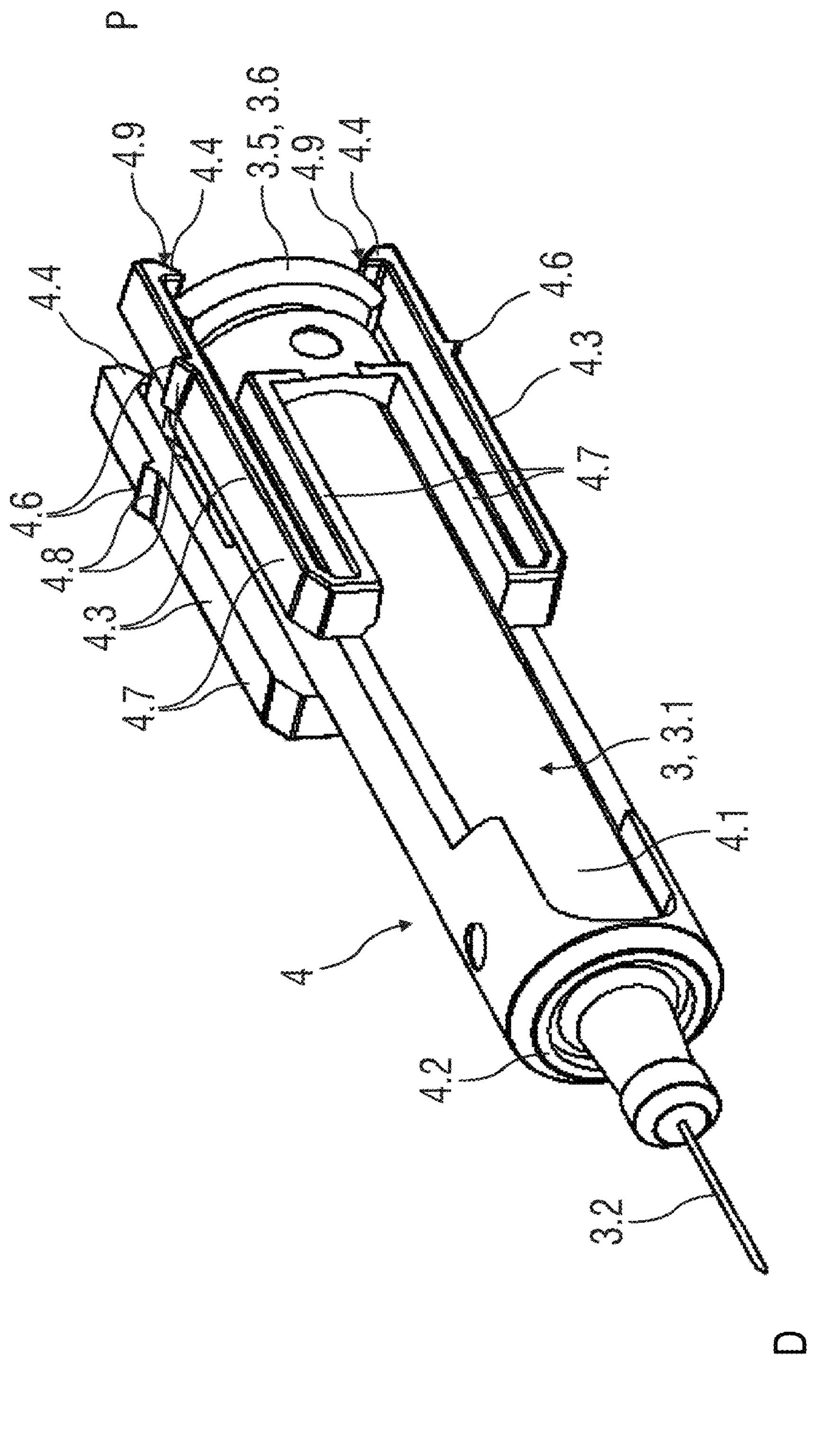
FIG. 5 is a schematic perspective view of an exemplary embodiment of a second medicament container coupled to an adapter according to the present invention.

In an exemplary embodiment, the adapter 4 may comprise at least one resilient arm 4.3 extending proximally and adapted to engage a proximal portion (e.g., the flange 3.5) of the container body 3.1. In the exemplary embodiment shown in FIG. 4, the adapter 4 includes four resilient arms 4.3. The arm 4.3 may include features to facilitate insertion and retention of the second medicament container 3. For example, a proximal end of the arm 4.3 may include a first ramp 4.9 which is adapted to engage the flange 3.5 (e.g., the straight section 3.7) when the second medicament container 3 is inserted into the adapter 4. As the flange 3.5 engages the first ramp 4.9, the arm 4.3 is deflected in a first radial direction until the flange 3.5 bypasses the ramped face 4.9. As shown in FIG. 5, when the arm 4.3 returns to a non-deflected position, a first abutment surface 4.5 may engage the flange 3.5 (e.g., straight section 3.7) and thereby prevent the second medicament container 3 from rotating relative to the adapter 4, and a second abutment surface 4.4 may abut a proximal face of the flange 3.5 and thereby prevent the second medicament container 3 from moving axially relative to the adapter 4.

Referring back to the exemplary embodiment shown in FIG. 4, the resilient arm 4.3 may include a second ramp 4.8, a third abutment surface 4.6, and a fourth abutment surface 4.7 which facilitate insertion and retention of the adapter 4 by the container carrier 1. For example, the second ramp 4.8 may be disposed on a radially outer surface of the arm 4.3. When the adapter 4 is inserted into the container carrier 1, the second ramp 4.8 may engage an element or an aperture 1.1 on the container carrier 1, which causes the arm 4.3 to deflect in a second radial direction (opposite the first radial direction) until the second ramp 4.8 bypasses the element. When the arm 4.3 returns to the non-deflected position, the third abutment surface 4.6 may engage a proximal stop in the container carrier 1 and thereby prevent axial displacement of the adapter 4 relative to the container carrier 1. The fourth abutment surface 4.7 may engage a surface or element in the container carrier 1 to prevent rotation of the adapter 4 relative to the container carrier 1.

Figure 6:
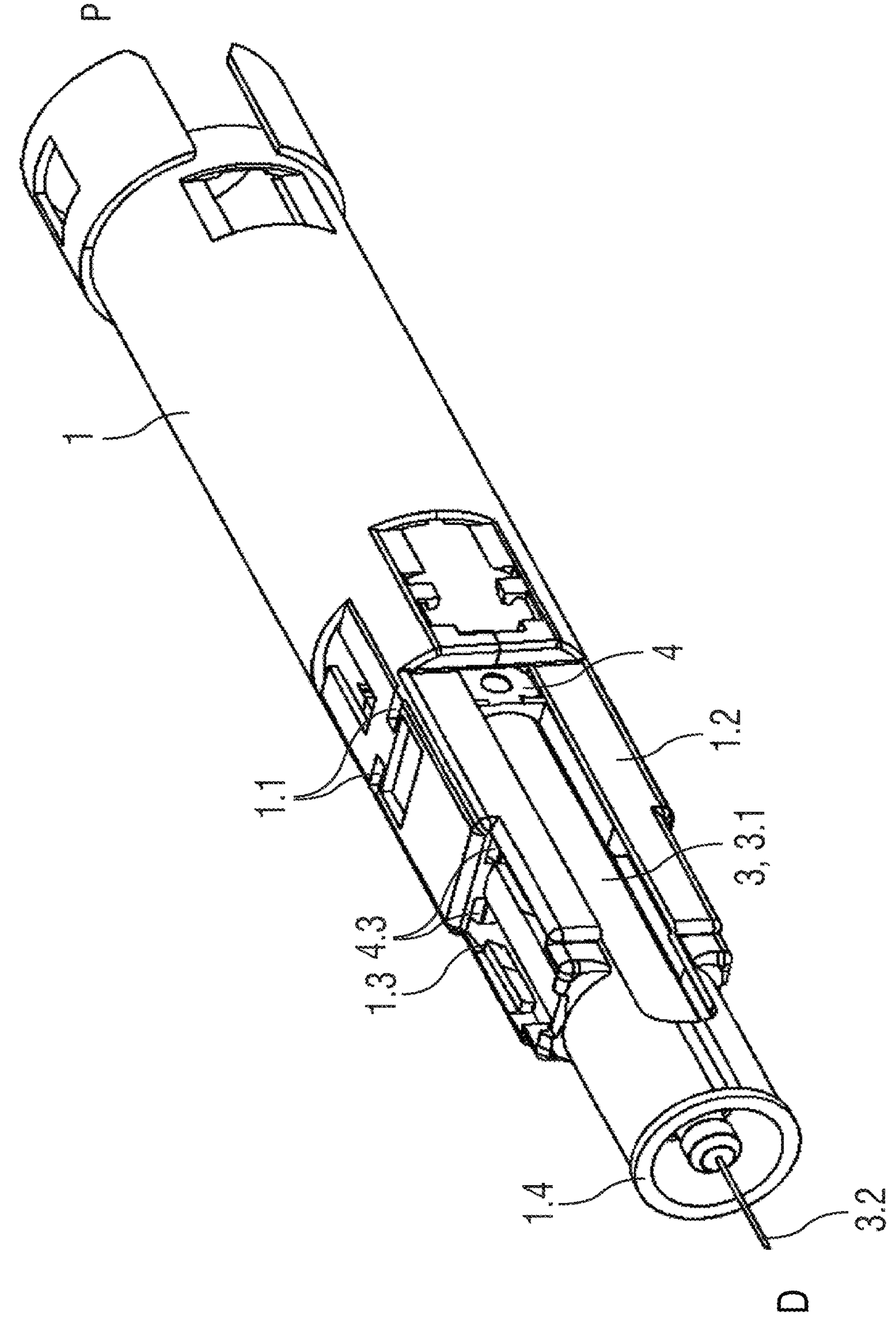
FIG. 6 is a schematic perspective view of an exemplary embodiment of a container carrier coupled to an adapter and a second medicament container according to the present invention.
Figure 7:
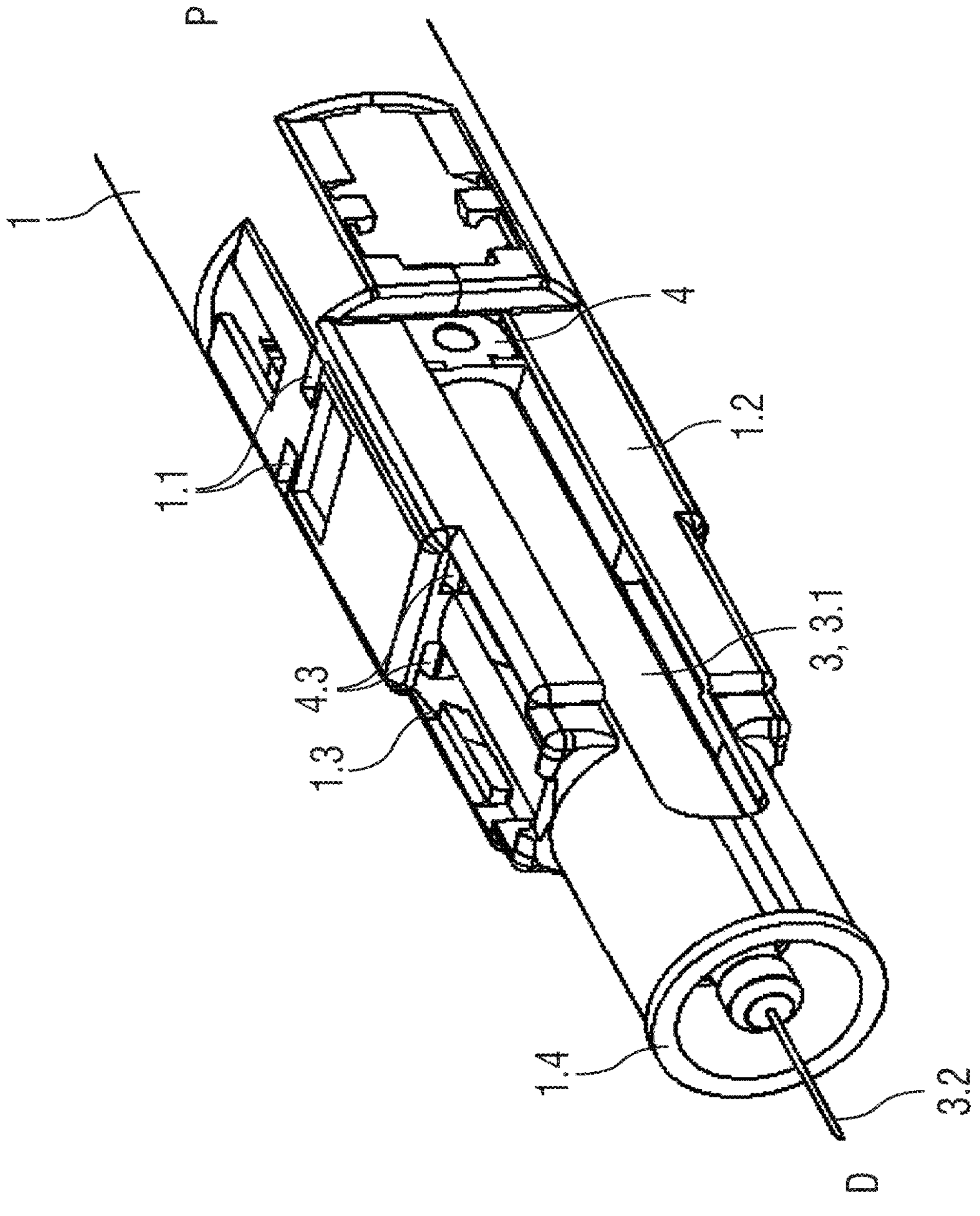
FIG. 7 is a schematic perspective detail view of an exemplary embodiment of a container carrier coupled to an adapter and a second medicament container according to the present invention.

The second medicament container 3 may be assembled with the container carrier 1 as shown in FIGS. 6 and 7 in at least two ways. In a first exemplary process, the adapter 4 may be inserted into the container carrier 1 and translated distally until it abuts a distal stop 1.3 and the third abutment surface 4.6 abuts proximal stop. The second medicament container 3 may then be inserted into the adapter 4 and translated distally until it abuts the distal rib 4.2 and the second abutment surface 4.4 abuts the flange 3.5. In a second exemplary process, the second medicament container 3 may be inserted into the adapter 4, and the adapter 4 may then be inserted into the container carrier 1.

In an exemplary embodiment, the first medicament container 2 may be adapted to contain greater than approximately 2 mL of a medicament, and the second medicament container may be adapted to contain less than approximately 2 mL of a medicament.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. An auto-injector comprising:
- a housing;
- a syringe carrier disposed in the housing; and
- a translucent syringe holder disposed in the syringe carrier, the translucent syringe holder comprising:
  - a distal portion configured to surround a portion of a barrel of a syringe and limit distal movement of the syringe relative to the translucent syringe holder when the syringe is disposed in the translucent syringe holder;
  - an axially-extending portion extending proximally from the distal portion, the axially-extending portion configured to surround a portion of a proximal flange of the syringe when the syringe is disposed in the translucent syringe holder, an outer surface of the axially-extending portion defining a first abutment surface engaged to an inner surface of the syringe carrier; and
  - a proximal portion extending radially inward from a proximal end of the axially-extending portion, the proximal portion defining a second abutment surface configured to engage diametrically opposite sides of the proximal flange of the syringe on a proximal side of the proximal flange of the syringe to limit proximal movement of the syringe relative to the translucent syringe holder when the syringe is disposed in the translucent syringe holder,
- wherein the translucent syringe holder is configured such that a distal side of the proximal flange is proximally spaced from the translucent syringe holder when the syringe is disposed in the translucent syringe holder.

2. The auto-injector of claim 1, wherein the translucent syringe holder is configured to limit relative rotation between the syringe and the syringe carrier when the syringe is disposed in the translucent syringe holder.

3. The auto-injector of claim 1, comprising the syringe disposed in the translucent syringe holder.

4. The auto-injector of claim 3, wherein the syringe contains a volume of medicament greater than 0 milliliters and less than 2 milliliters.

5. The auto-injector of claim 1, wherein the proximal flange of the syringe comprises one or more circular portions.

6. The auto-injector of claim 1, wherein the translucent syringe holder has a lateral opening.

7. An auto-injector comprising:
- a syringe carrier; and
- a translucent syringe holder configured to be disposed in the syringe carrier, the translucent syringe holder comprising:
  - a distal portion configured to surround a portion of a barrel of a syringe and limit distal movement of the syringe relative to the translucent syringe holder when the syringe is disposed in the translucent syringe holder;
  - an axially-extending portion extending proximally from the distal portion, the axially-extending portion configured to surround a portion of a proximal flange of the syringe when the syringe is disposed in the translucent syringe holder, an outer surface of the axially-extending portion defining a first abutment surface configured to engage an inner surface of the syringe carrier when the translucent syringe holder is disposed in the syringe carrier; and
  - a proximal portion extending radially inward from a proximal end of the axially-extending portion, the proximal portion defining a second abutment surface configured to engage diametrically opposite sides of the proximal flange of the syringe on a proximal side of the proximal flange of the syringe to limit proximal movement of the syringe relative to the translucent syringe holder when the syringe is disposed in the translucent syringe holder.

8. The auto-injector of claim 7, wherein the translucent syringe holder is configured such that a distal side of the proximal flange is proximally spaced from the translucent syringe holder when the syringe is disposed in the translucent syringe holder.

9. The auto-injector of claim 7, wherein the translucent syringe holder is configured to limit relative rotation between the syringe and the syringe carrier when the syringe is disposed in the translucent syringe holder.

10. The auto-injector of claim 7, wherein the proximal flange of the syringe comprises one or more arc sections.

11. The auto-injector of claim 7, comprising the syringe disposed in the translucent syringe holder.

12. The auto-injector of claim 11, wherein the syringe contains a volume of medicament greater than 0 milliliters and less than 2 milliliters.

13. The auto-injector of claim 7, wherein the translucent syringe holder has a lateral opening.

14. An auto-injector comprising:
- a syringe carrier having a distal end and a proximal end; and
- a translucent syringe holder disposed in the syringe carrier such that the proximal end of the syringe carrier is proximal to a proximal end of the translucent syringe holder, the translucent syringe holder configured to hold a syringe such that (i) rotational movement of the syringe relative to the syringe carrier is limited, and (ii) axial movement of the syringe relative to the translucent syringe holder is limited, the translucent syringe holder comprising a proximal portion configured to engage diametrically opposite sides of a proximal flange of the syringe to limit proximal movement of the syringe relative to the translucent syringe holder when the proximal flange of the syringe is disposed in the translucent syringe holder, wherein the auto-injector is configured such that a distal needle of the syringe is distal to the distal end of the syringe carrier when the syringe is disposed in the translucent syringe holder.

15. The auto-injector of claim 14, wherein the translucent syringe holder is configured such that a distal side of the proximal flange is proximally spaced from the translucent syringe holder when the syringe is disposed in the translucent syringe holder.

16. The auto-injector of claim 14, comprising the syringe disposed in the translucent syringe holder.

17. The auto-injector of claim 16, wherein the syringe contains a volume of medicament greater than 0 milliliters and less than 2 milliliters.

18. The auto-injector of claim 17, wherein the syringe is configured to dispense the volume of the medicament through the distal needle when a stopper advances distally along a barrel of the syringe.

19. The auto-injector of claim 14, wherein the proximal flange of the syringe comprises two arc sections connected by two straight sections.

20. The auto-injector of claim 14, wherein the translucent syringe holder comprises a distal portion configured to surround a portion of a barrel of the syringe when the syringe is disposed in the translucent syringe holder.

21. The auto-injector of claim 20, wherein the distal portion is configured to limit distal movement of the syringe relative to the translucent syringe holder when the syringe is disposed in the translucent syringe holder.

22. The auto-injector of claim 14, wherein the translucent syringe holder has a monolithic structure.

23. The auto-injector of claim 14, wherein an axial length of the syringe carrier is greater than an axial length of the translucent syringe holder.

24. A translucent syringe holder comprising:

a distal portion configured to surround a portion of a barrel of a syringe and limit distal movement of the syringe relative to the translucent syringe holder when the syringe is disposed in the translucent syringe holder;

an axially-extending portion extending proximally from the distal portion, the axially-extending portion configured to surround a portion of a proximal flange of the syringe when the syringe is disposed in the translucent syringe holder, an outer surface of the axially-extending portion defining a first abutment surface configured to engage an inner surface of a syringe carrier when the translucent syringe holder is disposed in the syringe carrier; and a proximal portion extending radially inward from a proximal end of the axially-extending portion, the proximal portion defining a second abutment surface configured to engage diametrically opposite sides of the proximal flange of the syringe to limit proximal movement of the syringe relative to the translucent syringe holder when the syringe is disposed in the translucent syringe holder.

25. The translucent syringe holder of claim 24, wherein the translucent syringe holder is configured such that a distal side of the proximal flange is proximally spaced from the translucent syringe holder when the syringe is disposed in the translucent syringe holder.

26. The translucent syringe holder of claim 24, wherein the syringe contains a volume of medicament greater than 0 milliliters and less than 2 milliliters.

27. The translucent syringe holder of claim 24, wherein the proximal flange of the syringe comprises one or more circular sections.

28. The translucent syringe holder of claim 27, wherein the one or more circular sections are connected by one or more straight sections.

29. The translucent syringe holder of claim 24, wherein the translucent syringe holder is configured to limit rotation of the syringe relative to the syringe carrier when the syringe is disposed in the translucent syringe holder and the translucent syringe holder is disposed in the syringe carrier.

30. The translucent syringe holder of claim 24, wherein the translucent syringe holder has a lateral opening.

* * * * *